United States Patent [19]

Gilligan et al.

[11] Patent Number: 5,196,599
[45] Date of Patent: Mar. 23, 1993

[54] METHOD OF PREPARING FLUORO, NITRO, AND FLUORONITROALKYL DIFLUOROFORMALS

[75] Inventors: William H. Gilligan, Ft. Washington; Michael E. Sitzmann, Adelphi, both of Md.

[73] Assignee: The United States of America as represented by the Secretary of the Navy, Washington, D.C.

[21] Appl. No.: 256,463

[22] Filed: Mar. 30, 1981

[51] Int. Cl.$^5$ .................... C07C 43/12; C07C 205/02
[52] U.S. Cl. .................................. 568/590; 149/88
[58] Field of Search ......................... 149/88; 260/463; 568/590, 594

[56] References Cited

U.S. PATENT DOCUMENTS 3,922,311  11/1975  Peters et al. ..................... 568/590

*Primary Examiner*—Richard D. Lovering
*Attorney, Agent, or Firm*—Kenneth E. Walden; Roger D. Johnson

[57] ABSTRACT

A method of preparing difluoroformals of the formula $$(RCH_2O)_2CF_2,$$

wherein R is $-C(NO_2)_3$, $-CF(NO_2)_2$, $-CF_2(NO_2)$, $-C(NO_2)_2CH_3$, or a fluoroalkyl group such as $-CF_3$ or $-CF_2CF_3$, by reacting the corresponding dichloroformals with hydrogen fluoride in pyridine. These difluoroformals are useful as energetic explosive and propellant ingredients.

3 Claims, No Drawings

METHOD OF PREPARING FLUORO, NITRO, AND FLUORONITROALKYL DIFLUOROFORMALS

BACKGROUND OF THE INVENTION

This invention relates to organic compounds and more particularly to difluoroformals.

U.S. Pat. No. 3,922,311, entitled "Fluorodinitroethyl Difluoroformal and Process of Manufacture," which was issued to Howard M. Peters and Robert L. Simon, Jr., on Nov. 25, 1975, discloses the synthesis of bis(2-fluoro-2,2-dinitroethyl) difluoroformal by the reaction of bis(2-fluoro-2,2-dinitroethyl) carbonate with sulfur tetrafluoride and hydrogen fluoride. Similar compounds have been prepared at SRI International, 333 Ravenswood Avenue, Menlo Park, Calif. 94025, by the reaction of carbonates and thionocarbonates with sulfur tetrafluoride with catalysts such as $TiCl_4$ using in at least some cases liquid hydrogen fluoride as solvent. The reaction is conducted in high pressure equipment for extended periods of time (10–25 days) at temperature $\geq 100°$. Workup requires the removal of noxious gasses and reactant and catalyst impurities. In addition difficult purification of the product is often required. Yields are on the order of 70–90%. It would be desirable to provide an easier method of preparing fluoro-, nitro-, and fluoronitroalkyl difluoroformals.

SUMMARY OF THE INVENTION

Accordingly, an object of this invention is to provide an improved method of synthesizing fluoro-, nitro-, and fluoronitroalkyl difluoroformals.

Another object of this invention is to provide a method of synthesizing fluoro-, nitro-, and fluoronitroalkyldifluoro formals at ambient temperature and pressure.

A further object of this invention is to provide a faster method of synthesizing fluoro-, nitro-, and fluoronitroalkyl difluoroformals.

These and other objects of this invention are achieved by providing a method of preparing difluoroformals of the formula

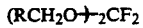

wherein R is $-C(NO_2)_3$, $-CF(NO_2)_2$, $-CF_2(NO_2)$, $-C(NO_2)_2CH_3$, $-CF_3$, and $-CF_2CF_3$, comprising:

(1) adding a dichloroformal of the formula

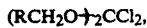

wherein R is as defined above, to a solution of hydrogen fluoride in pyridine and allowing the dichloroformal to react with the hydrogen fluoride to give the difluoroformal; and (2) isolating the product difluoroformal.

The difluoroformals are useful as energetic explosive and propellant ingredients.

DETAILED DESCRIPTION OF THE PREFERRED EMBODIMENT

Methods of preparing the dichloroformals used in this invention are disclosed in the U.S. Patent Application Ser. No. 256,462 filed Mar. 30, 1981 entitled "Polynitroethyl Dichloroformals," by William H. Gilligan, filed concurrently with the present application, herein incorporated by reference. The dichloroformals are prepared by refluxing the corresponding thionocarbonate with sulfuryl chloride in the presence of a catalytic amount of either $AlCl_3$ or $TiCl_4$. Another method is to pass chlorine gas through a mixture of the thionocarbonate, a chlorinated hydrocarbon (e.g., $CCl_4$, $CHCl_3$, $CH_2Cl_2$, or 1,2-dichloroethane), and a polar additive (e.g., 2,2,2-trifluoroethanol or acetonitrile). Preferably, at least two moles of polar additive is used for each mole of thionocarbonate. The reaction temperature for this second method is preferably from 15° to 25° C. (with a reaction time of from 3 to 8 hours).

Dichloroformals which are used include,

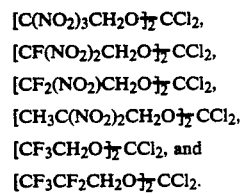

The difluoroformals which are produced include

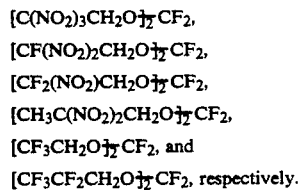

The reaction is carried out by adding the dichloroformal to a solution of hydrogen fluoride in pyridine and stirring at ambient temperatures, and pressure for from 1 to 3 days. Preferably a 60 to 70% by weight solution of HF in pyridine is used. The reaction appears to be complete in a day or less, though to ensure complete reaction, longer times were sometimes used. The product is isolated by pouring into water and extracting with an immiscible organic solvent such as methylene chloride. After drying and removal of the solvent, the product is obtained in essentially quantitative yield and is essentially analytically pure. The dichloroformal can be added either in the neat state or in a solution of methylene chloride or 1,2-dichloroethane. The reaction solution can be heated to 50° but there is no advantage in so doing.

To more clearly illustrate this invention, the following examples are presented. It should be understood, however, that these examples are presented merely as a means of illustration and are not intended to limit the scope of the invention in any way.

EXAMPLES

The reactions in Examples 1 through 5 were carried out by adding the appropriate dichloroformal to a 60–70% solution of hydrogen fluoride in pyridine and stirring the solution at ambient temperature. The product difluoroformals were isolated by pouring the reaction solution into water and then extracting out the product difluoroformal with a water-immiscible solvent such as methylene chloride. After drying and removal of the solvent, the products were obtained in essentially quantitative yield and were essentially analytically pure.

Table 1 presents a summary for Examples 1–5 of the starting materials, reaction times, products, and yields.

Table 2 presents the elemental analyses of the product difluoroformals of Examples 1-5.

Obviously, many modifications and variations of the present invention was possible in light of the above teachings. It is therefore to be understood that within the scope of the appended claims the invention may be practiced otherwise than as specifically described.

TABLE 1

| (RCH$_2$O)$_2$ CCl$_2$ | | wt. of dichloro-formal (g) 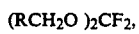 HF/pyridine | (RCH$_2$O)$_2$CF$_2$ ml, HF/pyridine | Time (hr) | Yield (%) | H-NMR(CDCl$_3$)TMS) (ppm) |
|---|---|---|---|---|---|---|
| Example No. | R | | | | | |
| 1 | C(NO$_2$)$_3$ | 3.48 | 10 | 20 | 98 | 5.12 (s) |
| 2 | FC(NO$_2$)$_2$ | 5.0 | 10 | 20 | ~100 | 4.97 (d) |
| 3 | F$_2$C(NO$_2$) | 3.79 | 8 | 16 | 97 | 4.58 (t) |
| 4 | CH$_3$C(NO$_2$)$_2$ | 2.53 | 7.5 | 16 | ~100 | 4.68 (s); 2.23 (s) |
| 5 | CF$_3$ | 9.6 | 15 | 16 | 72* | 4.22 (q) |

*minimum yield because of mechanical losses.

TABLE 2

| | | Elemental Analyses | | | | |
|---|---|---|---|---|---|---|
| Example No. | R | | % C | % H | % N | % F |
| 1 | C(NO$_2$)$_3$ | Calc. | 14.64 | 0.98 | 20.49 | 9.26 |
| | | Found | 14.73 | 1.00 | 20.28 | 9.02 |
| 2 | FC(NO$_2$)$_2$ | Calc. | 16.86 | 1.13 | 15.73 | 21.34 |
| | | Found | 16.82 | 1.12 | 15.49 | 21.16 |
| 3 | F$_2$C(NO$_2$) | Calc. | 19.88 | 1.33 | 9.27 | 37.74 |
| | | Found | 19.98 | 1.30 | 9.39 | 37.46 |
| 4 | CH$_3$C(NO$_2$)$_2$ | Calc. | 24.15 | 2.90 | 16.09 | 10.91 |
| | | Found | 24.08 | 2.97 | 15.49 | 10.71 |
| 5 | CF$_3$ | Calc. | 24.21 | 1.62 | — | 61.27 |
| | | Found | 23.99 | 1.61 | — | 61.09 |

We claim:

1. A method of preparing a difluoroformal of the formula (RCH$_2$O)$_2$CF$_2$, wherein R is selected from the group consisting of —C(NO$_2$)$_3$, —CF(NO$_2$)$_2$, —CF$_2$(NO$_2$), —C(NO$_2$)$_2$CH$_3$, —CF$_3$, and —CF$_2$CF$_3$, comprising:

(1) adding a dichloroformal of the formula (RCH$_2$O)$_2$ CCl$_2$, wherein R is as defined above, to a solution of hydrogen fluoride in pyridine and allowing the dichloroformal to react with the hydrogen fluoride to give the difluoroformal; and (2) isolating the product difluoroformal.

2. The method of claim 1 wherein R is selected from the group consisting of —C(NO$_2$)$_3$, —CF(NO$_2$)$_2$, —CF$_2$(NO$_2$), —C(NO$_2$)$_2$CH$_3$, and —CF$_3$.

3. The method of claim 1 or 2 wherein the solution of hydrogen fluoride in pyridine comprises from about 60 to about 70 weight percent of hydrogen fluoride in pyridine.

* * * * *